United States Patent [19]
Mitchell

[11] Patent Number: 5,481,852
[45] Date of Patent: Jan. 9, 1996

[54] METHOD AND APPARATUS TO PROMOTE GAS EXCHANGE FROM A SEALED RECEPTACLE

[75] Inventor: Jerry L. Mitchell, Livingston, Tex.

[73] Assignee: Pakor, Inc., Livingston, Tex.

[21] Appl. No.: 101,235

[22] Filed: Jun. 24, 1993

Related U.S. Application Data

[63] Continuation-in-part of Ser. No. 649,583, Feb. 1, 1991, abandoned, which is a continuation-in-part of Ser. No. 510,938, Apr. 19, 1990, abandoned, which is a continuation-in-part of Ser. No. 214,195, Jun. 27, 1988, Pat. No. 4,919,955, which is a division of Ser. No. 94,384, Sep. 8, 1987, abandoned.

[51] Int. Cl.[6] .................................................. B65B 31/02
[52] U.S. Cl. .............. 53/432; 53/510; 426/129; 426/316; 426/418
[58] Field of Search ................. 53/86, 89, 128.1, 53/510, 511, 512, 432; 141/4, 8, 51, 66; 426/129, 315, 316, 410, 418

[56] References Cited

U.S. PATENT DOCUMENTS

| | | | |
|---|---|---|---|
| 1,148,823 | 8/1915 | Bocande | 426/316 |
| 1,591,932 | 7/1926 | Young | 141/4 X |
| 1,914,121 | 6/1933 | Hamersley | 426/316 |
| 2,862,528 | 12/1958 | Geisler | 53/510 X |
| 3,421,836 | 1/1969 | Sundin et al. | 426/418 X |
| 3,693,314 | 9/1972 | Reid et al. | 53/512 X |
| 4,294,859 | 10/1981 | Lundquist et al. | 426/129 X |
| 4,744,199 | 5/1988 | Gannon | 53/512 X |
| 4,779,398 | 10/1988 | Glandon et al. | 53/512 X |
| 4,909,014 | 3/1990 | Kobayashi et al. | 53/510 X |

*Primary Examiner*—Linda Johnson
*Attorney, Agent, or Firm*—Sankey & Luck

[57] ABSTRACT

The method and apparatus for exchanging gases contained within a sealed container is disclosed, said system comprising a pressurizable housing through which sealed container is passed, means to affix a valve to said container and means to exchange gases through said valve.

27 Claims, 13 Drawing Sheets

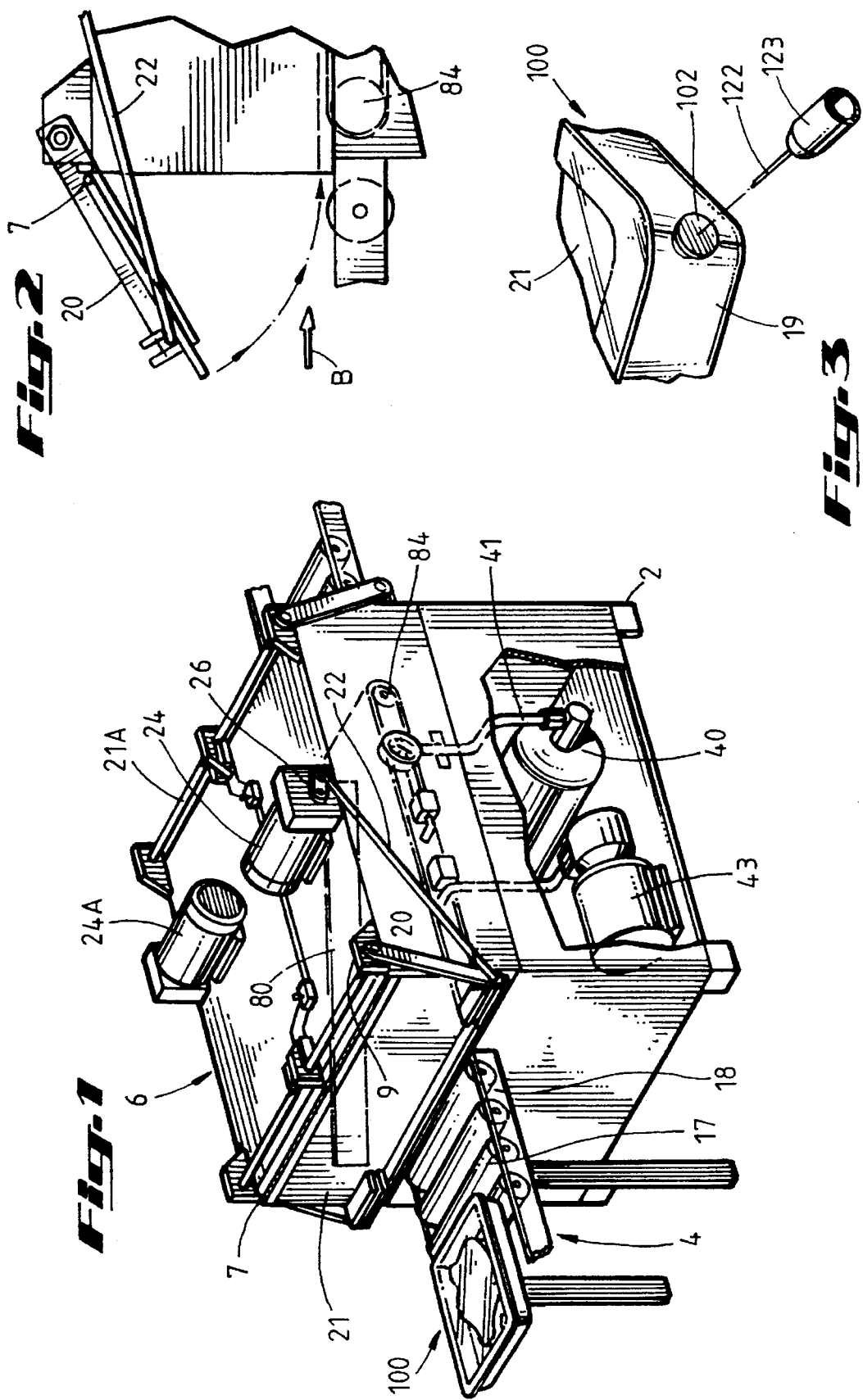

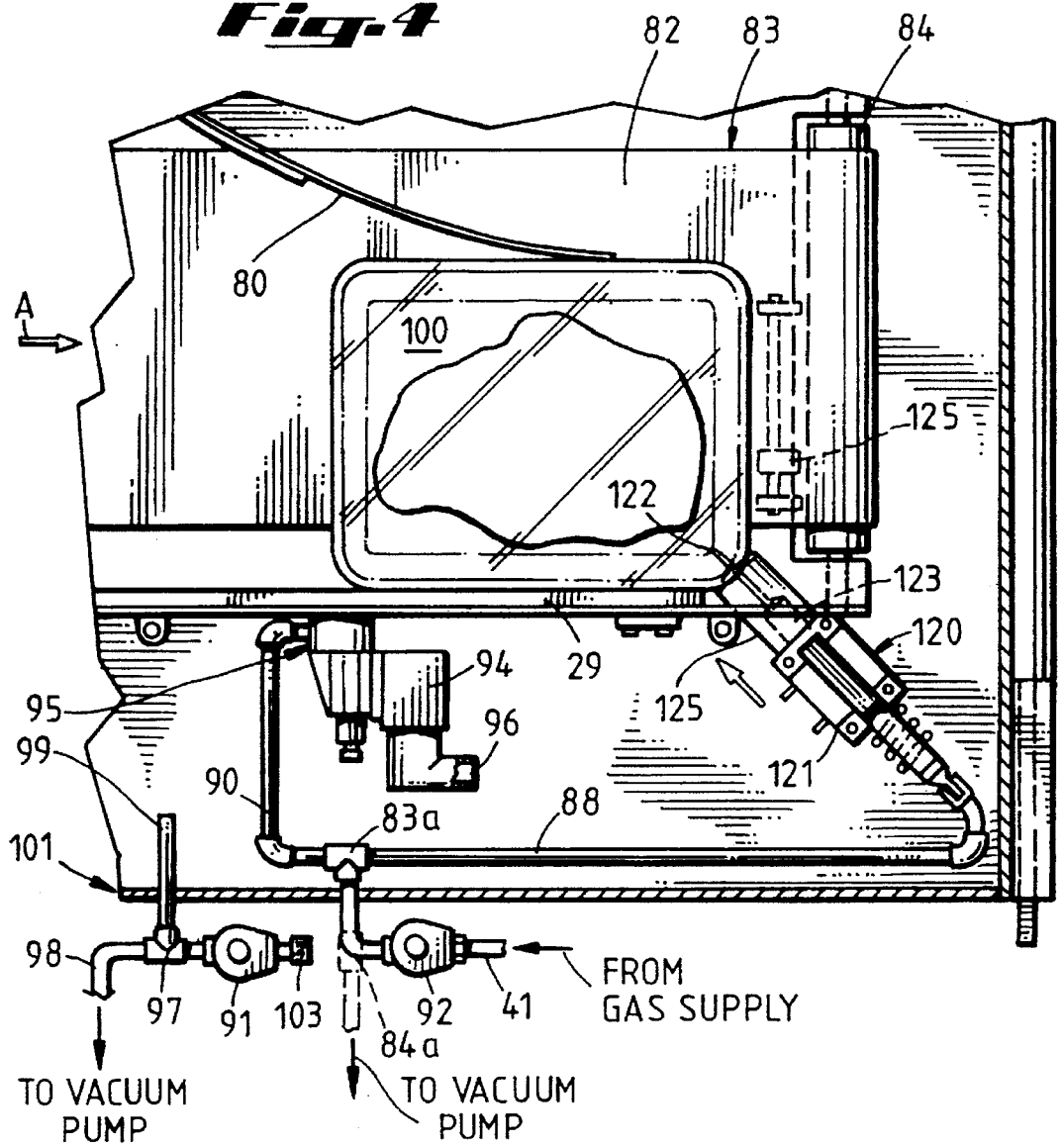
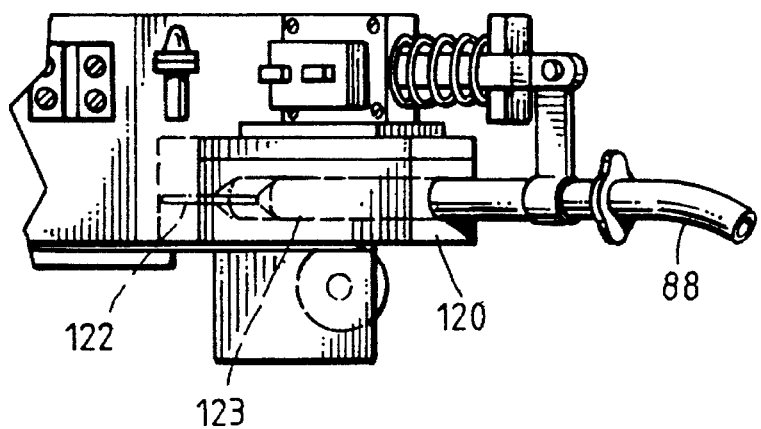

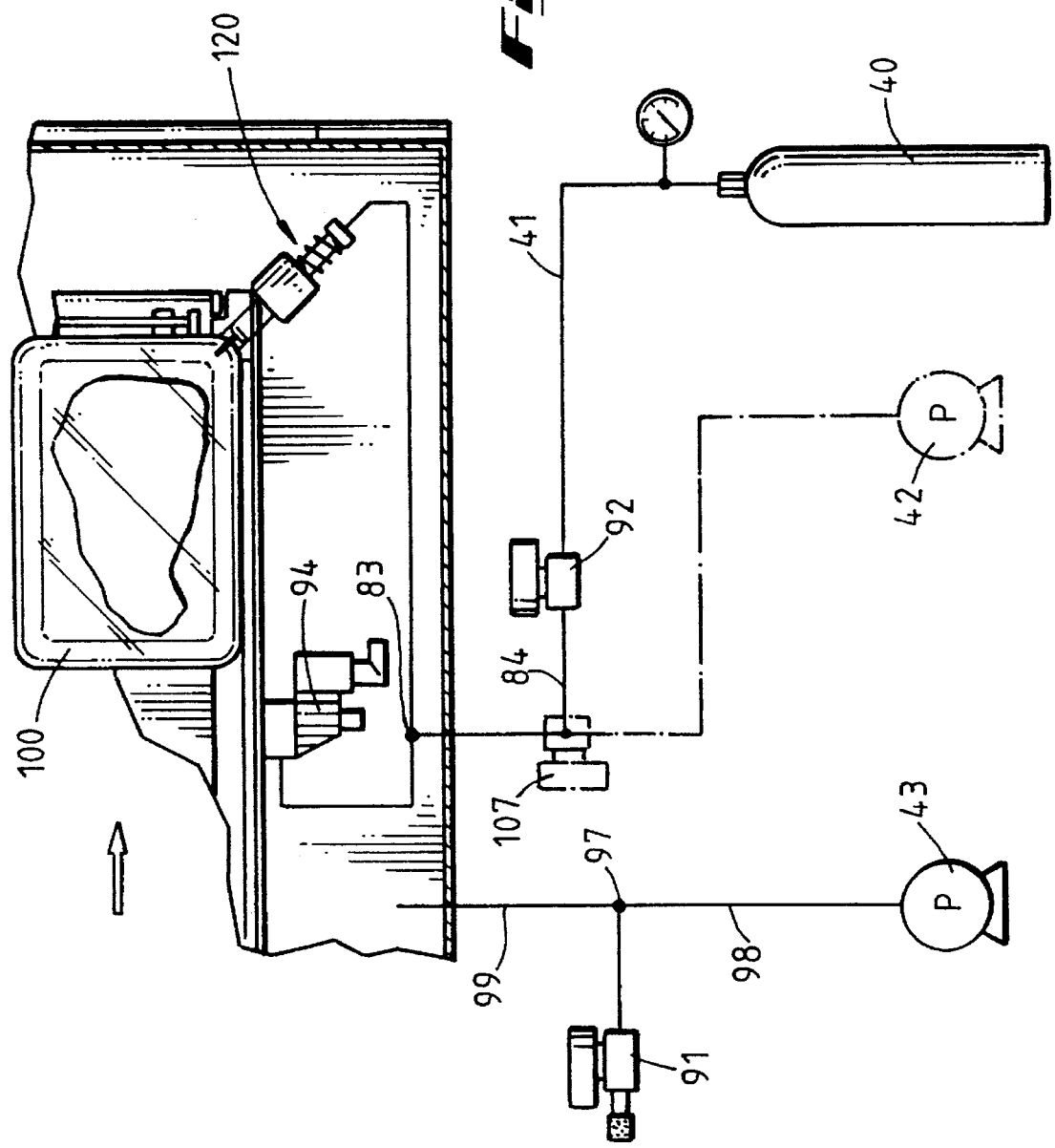

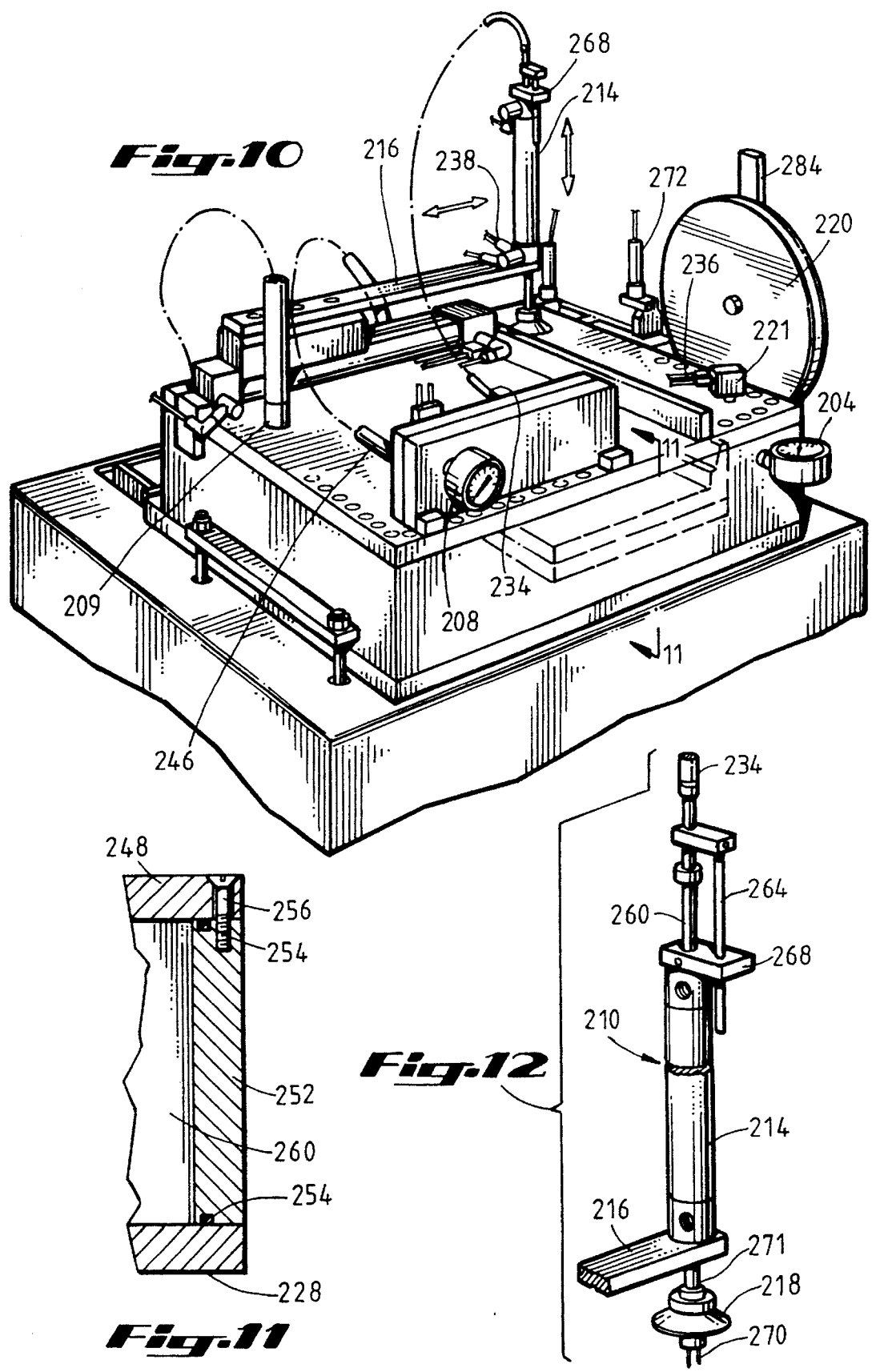

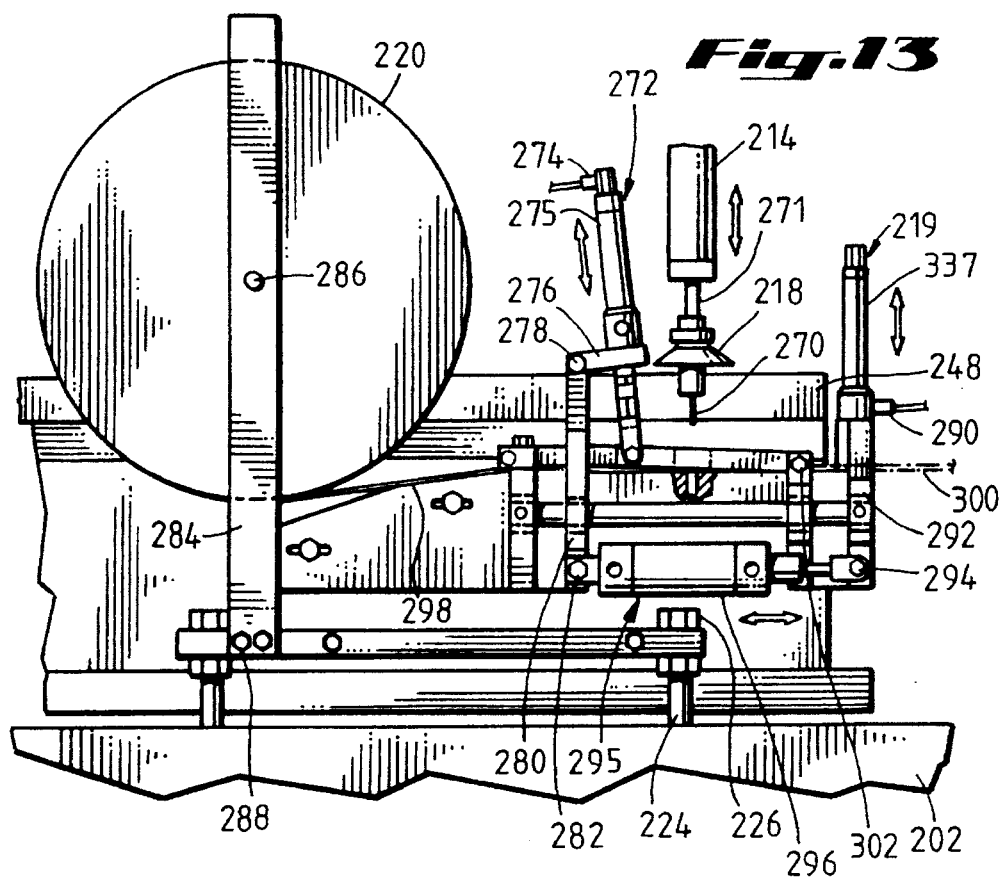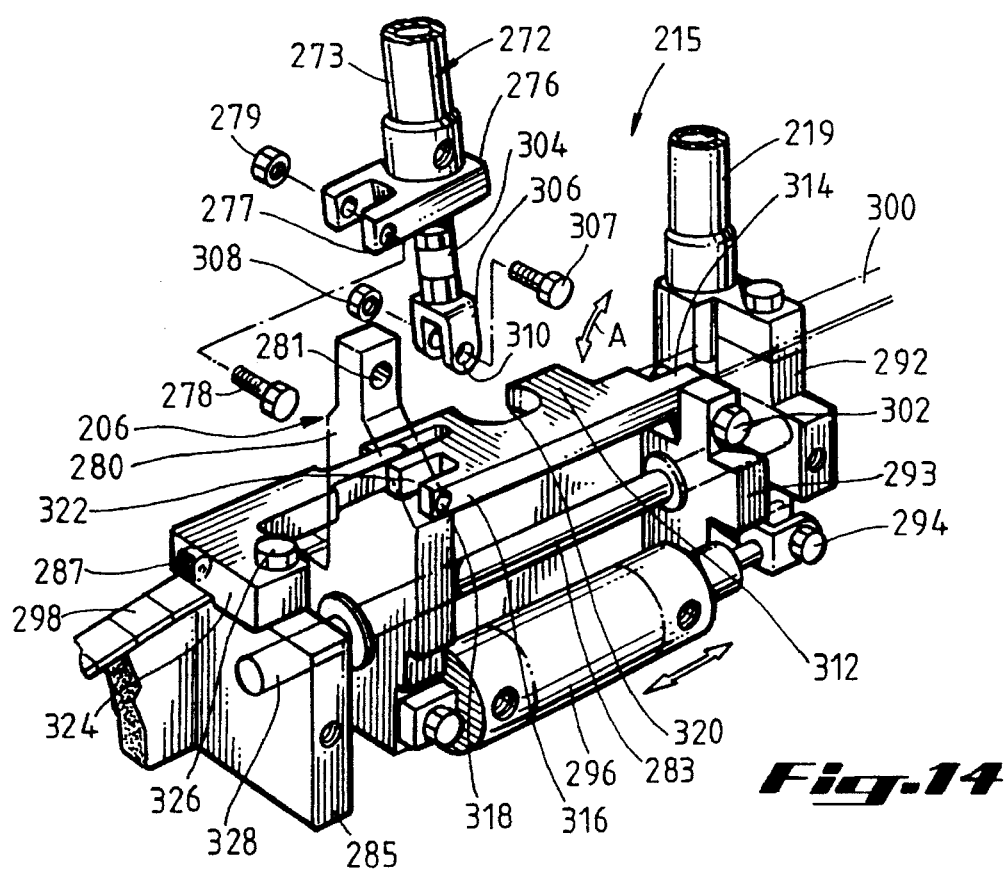

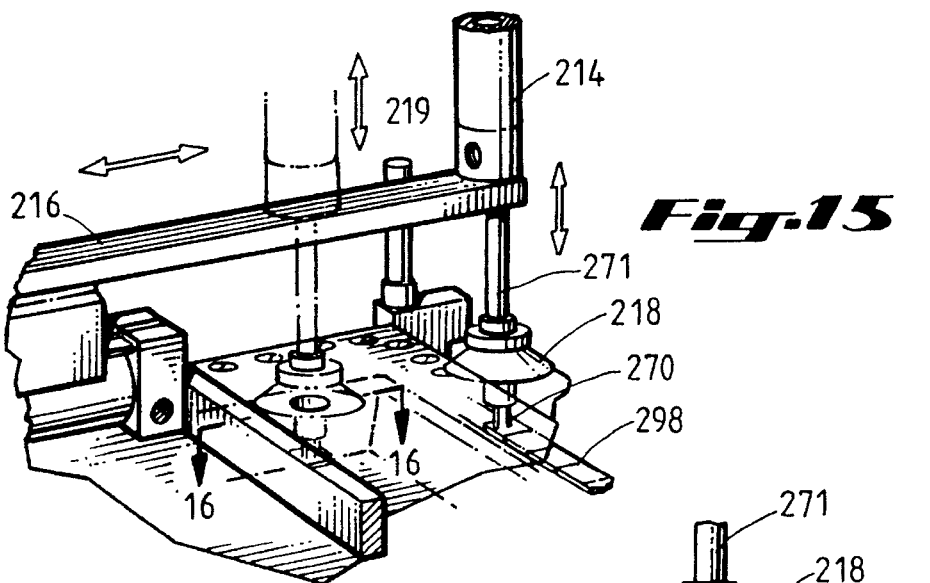
Fig. 15
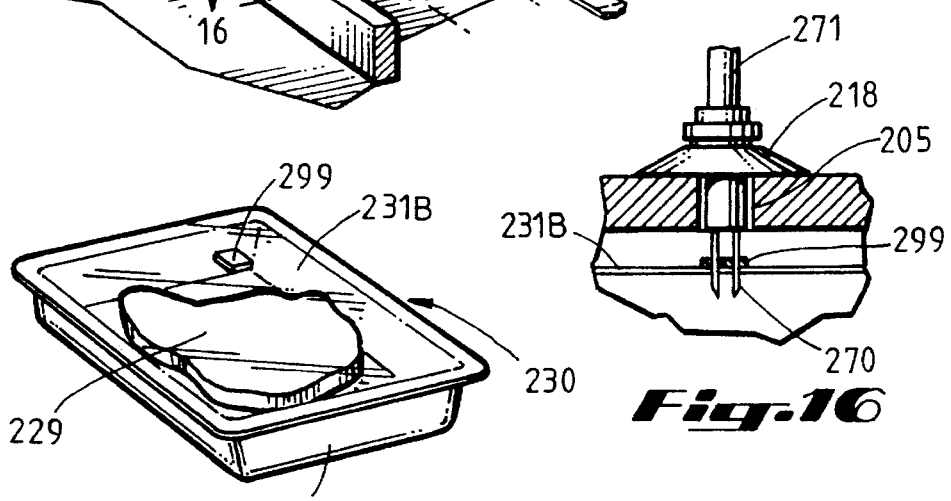
Fig. 17
Fig. 16
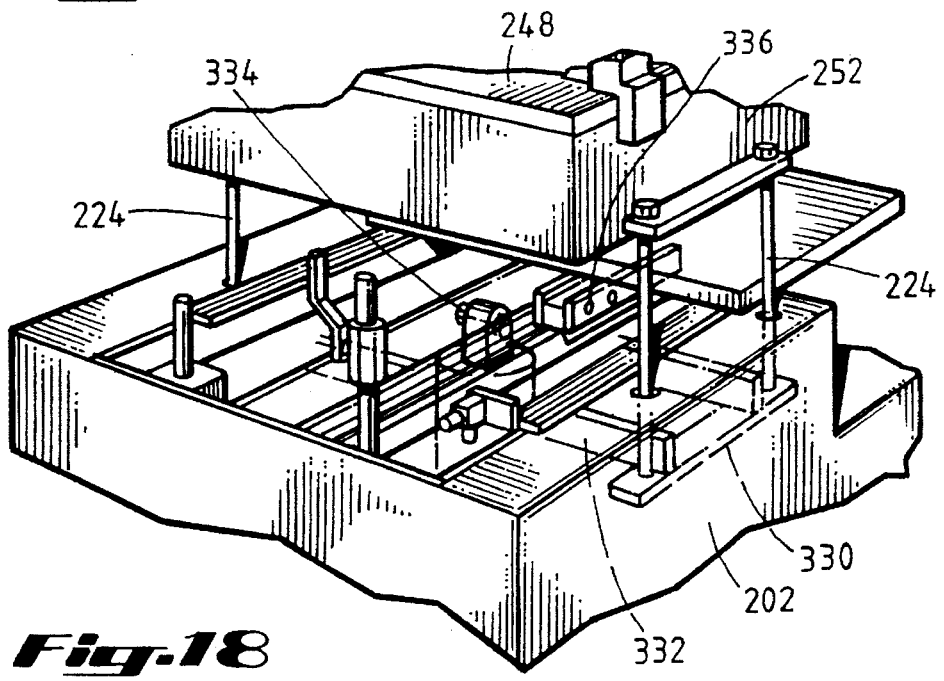
Fig. 18

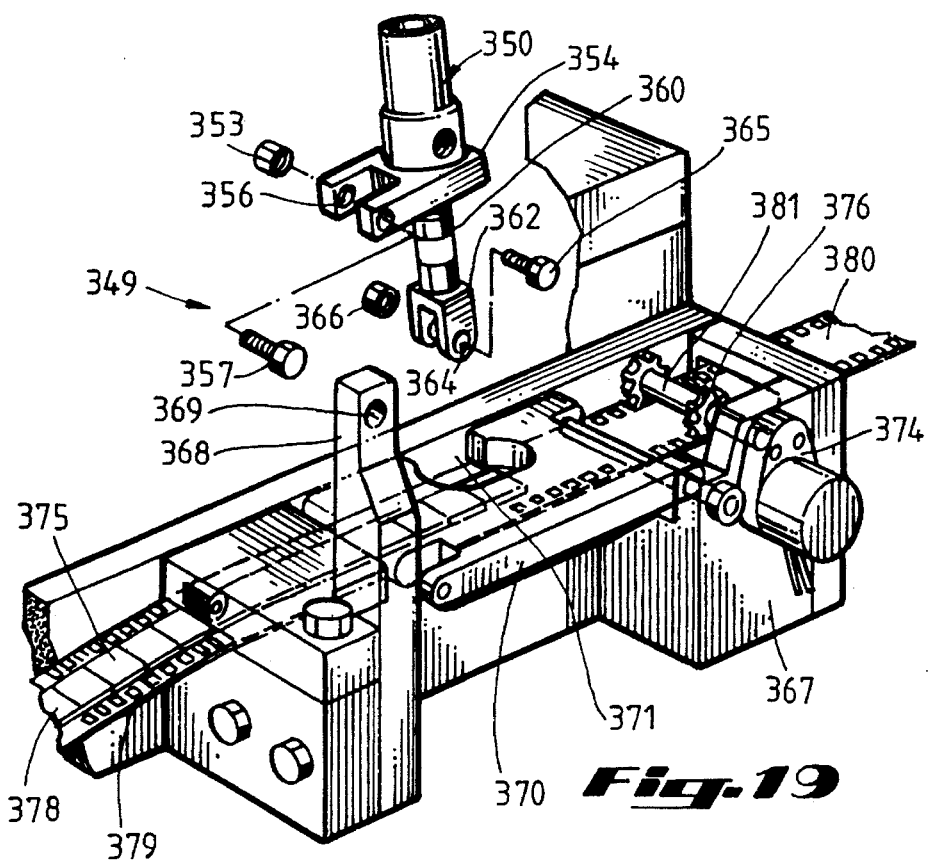
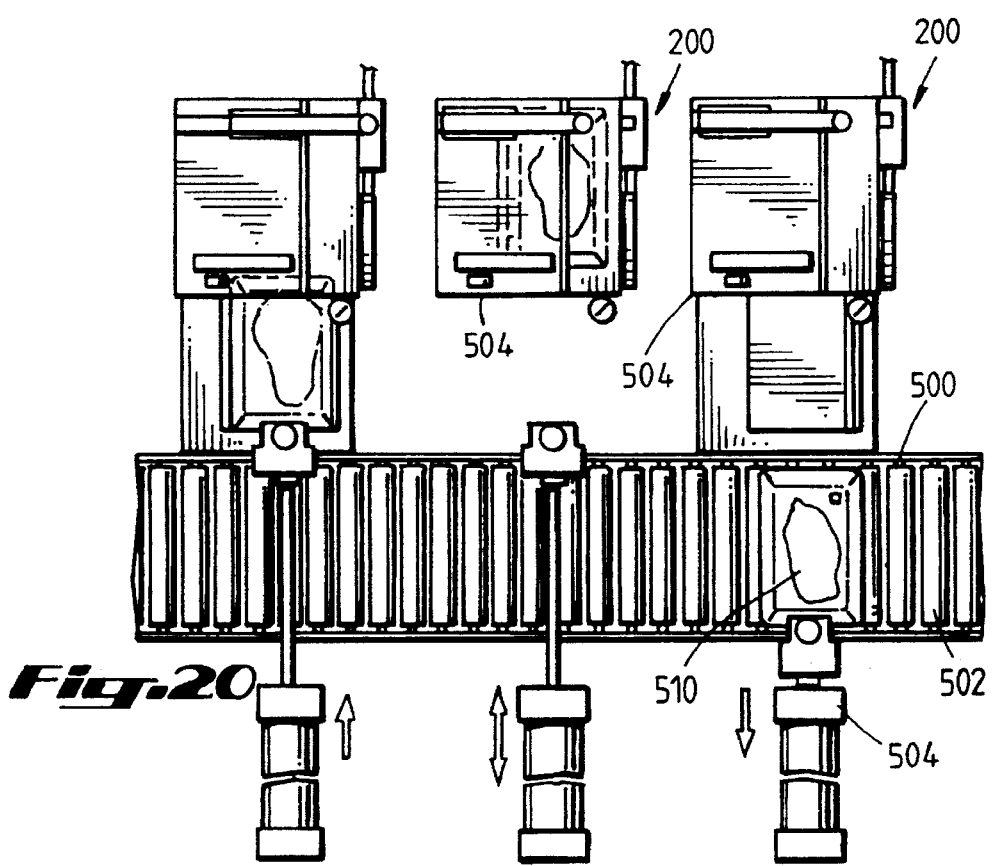

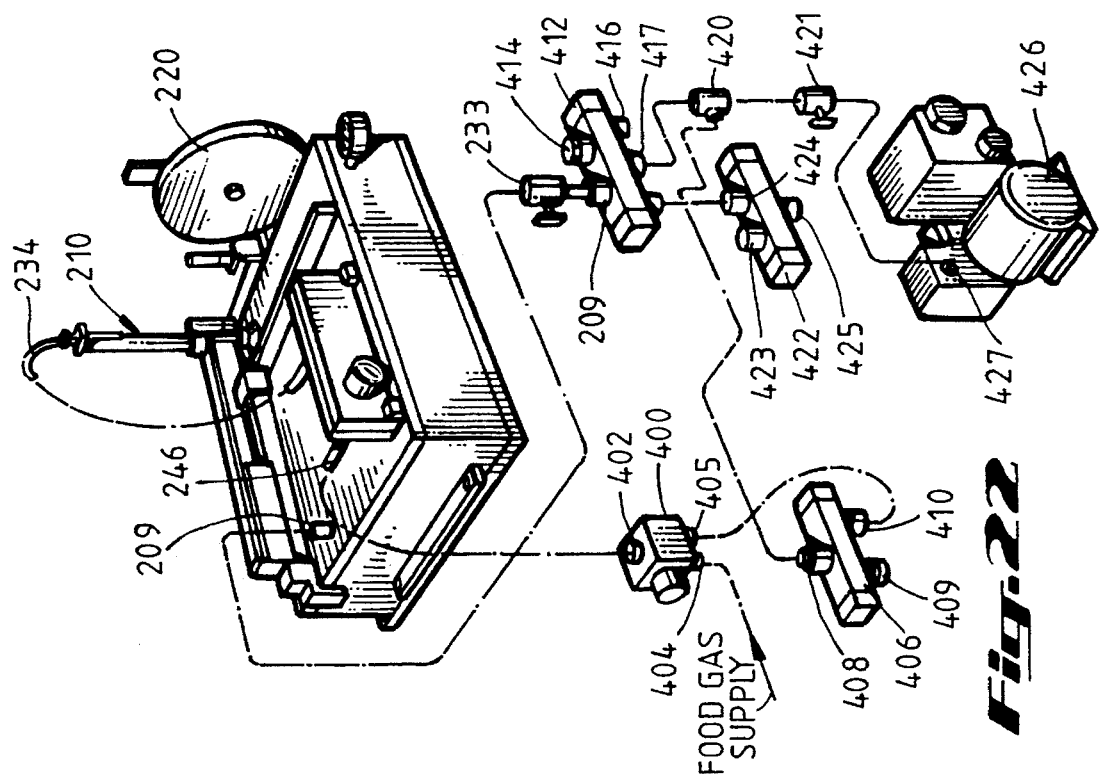
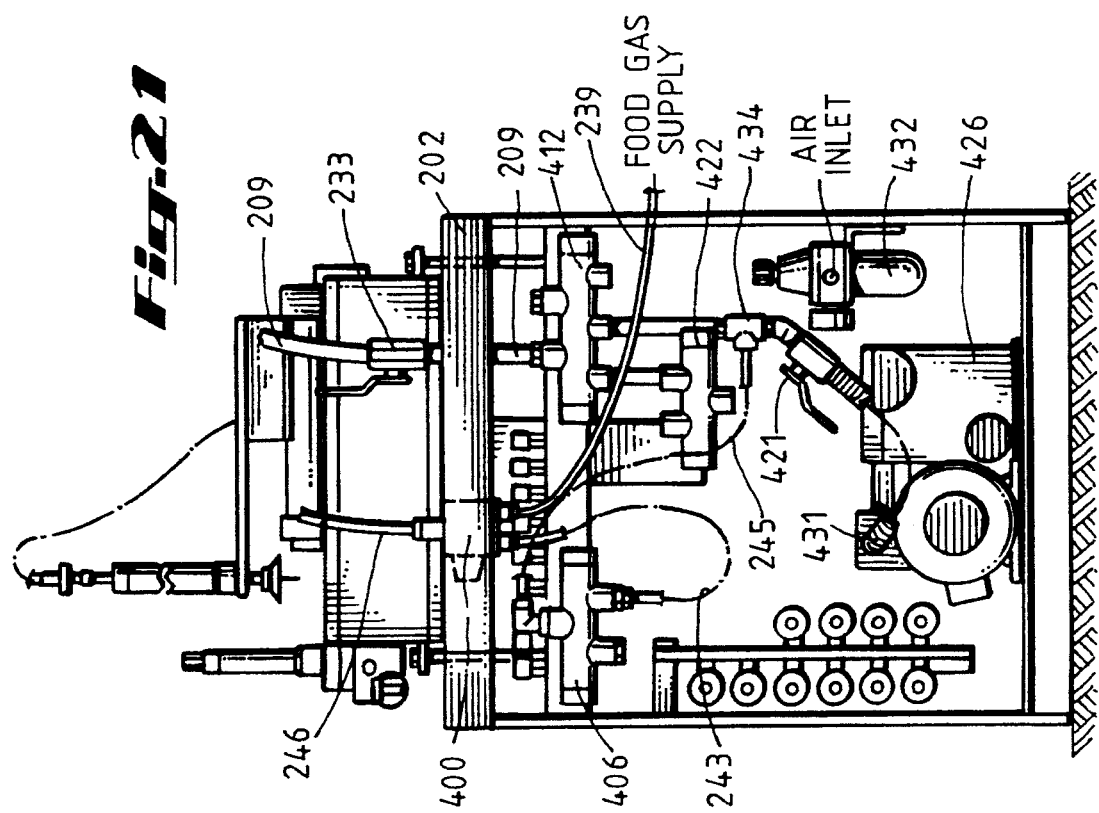

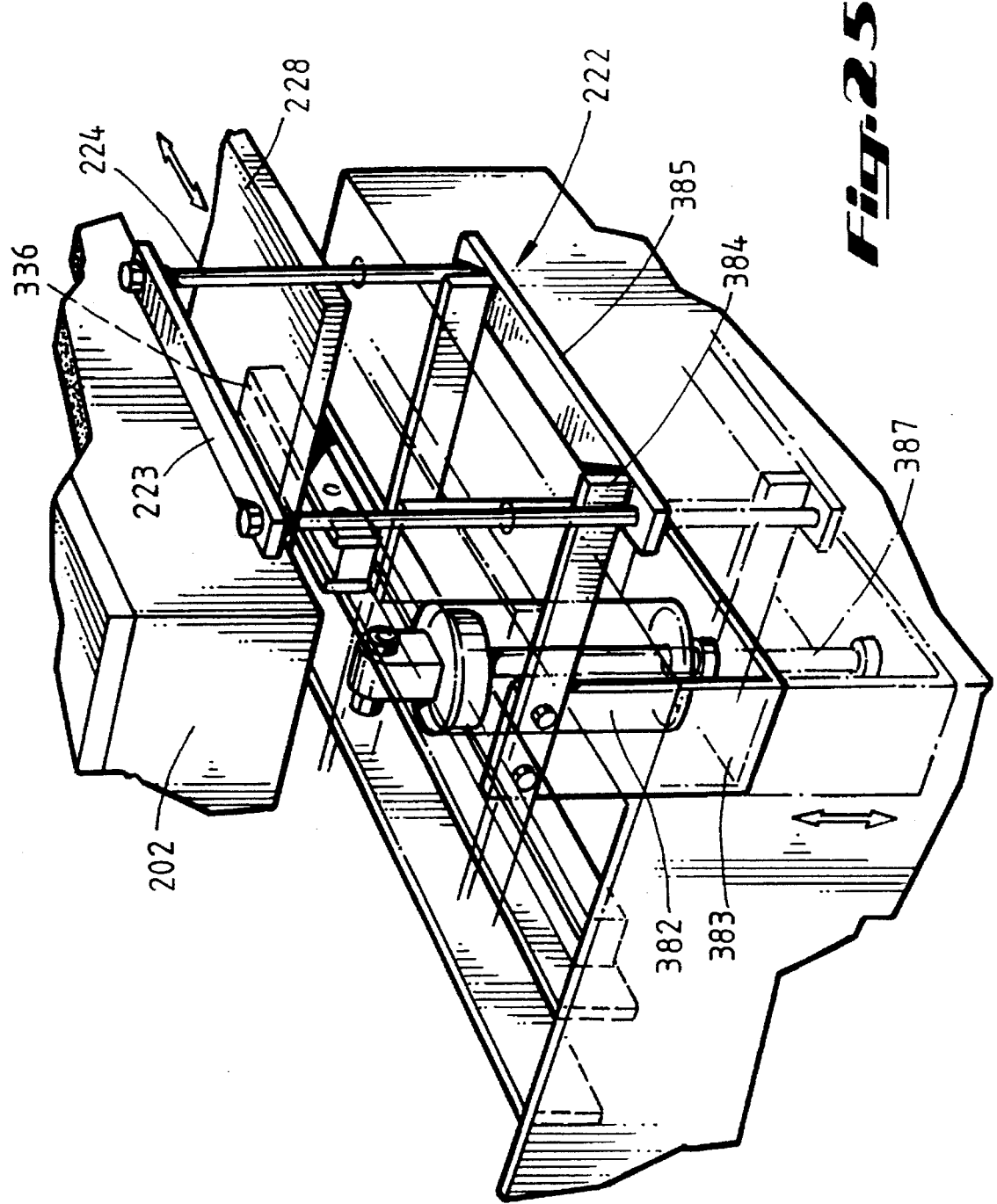

METHOD AND APPARATUS TO PROMOTE GAS EXCHANGE FROM A SEALED RECEPTACLE

This application is a continuation-in-part of application Ser. No. 649,583 filed Feb. 1, 1991, now abandoned, which represents a continuation-in-part of application Ser. No. 510,938, filed Apr. 19, 1990, now abandoned, which is a continuation-in-part of pending application Ser. No. 214, 195, filed Jun. 27, 1988, now U.S. Pat. No. 4,919,955, which is a divisional of application Ser. No. 94,384, filed Sept. 8, 1987, now abandoned. The disclosure of the aforementioned applications is herein incorporated by reference.

BACKGROUND OF THE INVENTION

1. Field of the Invention

The present invention relates to a method and apparatus for modifying the gaseous atmosphere in a sealed receptacle containing a deteriorative material or a material of which controlled fluid exposure is desired. In a preferred embodiment, the present invention is directed to a method and apparatus for extracting, modifying, or exchanging the gases within a closed, sealed receptacle, while inhibiting the structural collapse of the receptacle. The invention is especially concerned with treating foods in the original flexible packages in which the foods are initially wrapped for purposes of transport, display and marketing.

2. Description of the Prior Art

The shelf life of many food products at both a refrigerated state and at room temperature can be greatly extended if the food product is placed in a substantially oxygen free environment. One way of achieving this oxygen free environment is to evacuate a package containing the food product to a very high level of vacuum. However, when flexible packaging is involved, as is often the case in consumer ready packaging, the use of a high vacuum can distort, compact and crush the enclosed product as the vacuum is applied. For example, bakery products can readily be squeezed or compressed so that they lose their consumer appeal. Shredded cheeses can be compacted to such an extent that they require reshredding. Fruit products can be bruised with a resultant loss of both appearance and flavor.

Meat, fruit and vegetable products subjected to vacuum packing can also undergo liquid purge which diminishes their appearance and flavor. Additionally, meat products subjected to vacuum packaging often adopt a purplish color since no oxymyoglobin is formed due to the lack of oxygen. This color is sometimes unacceptable for domestic retail marketing, and hence the product must be removed from the vacuum package prior to display and repackaged in a way so as to allow the characteristic red "bloom" to appear in the meat product.

To overcome the aforedescribed disadvantages, gas packaging has been used as an alternative to vacuum packing. Gas packaging entails a modification of the atmosphere within the receptacle housing the product so as to introduce a growth inhibiting agent, i.e. an inert gas, or an oxygenating agent, into the receptacle. As disclosed in applicant's copending application Ser. No. 214,195, it may also be desirable to modify the gas within the receptacle to include a desired concentrations of an oxidizing agent, e.g. ozone, so as to reduce or eliminate bacterial concentration within the receptacle.

In instances where gas flush packaging is utilized, it is often desirable to remove a substantial portion of the original, resident atmosphere within the receptacle before introducing a second gas or combination of gases. This is desirable so as to decrease the amount of the secondary gas necessary to beneficially affect the containerized product. If evacuation or partial evacuation of the receptacle is not first undertaken, the secondary gas will be diluted and will therefore be required in greater quantities or concentrations in order to achieve its intended purpose. At least partial gas extraction is therefore desirable in order to remove the resident gas preliminary to the introduction of a second gas. This gas extraction, however, if conducted in a conventional manner, will also bring about the disadvantages noted above in connection with vacuum packaging in that the package will undergo distortion or collapse.

A variety of devices have been developed to address the problems associated with the collapse of a flexible container or receptacle during gas exchange or extraction. One such device is seen in U.S. Pat. No. 1,591,932 (the '932 patent) as issued to Young. The '932 patent discloses a method and apparatus for replacing air in a filled container with an inert gas. In the '932 patent, the receptacle is placed within a vacuum chamber and the pressures inside and outside the receptacle regulated so as to avoid the deformation or collapse of the walls of the receptacle. Gas exchange in the '932 patent is accomplished by withdrawing the resident atmosphere from the receptacle via a vent hole while maintaining an equal pressure within the vacuum chamber. When the addition of the inert gas is desired, pressure equalization is accomplished via a yoke which is activated by the pressure of the gas injected into the receptacle.

Disadvantages of the apparatus disclosed in the '932 patent include the need to form an aperture in the container in order to achieve evacuation and repressurization in addition to the need to utilize a secondary sealing step to maintain the second atmosphere within the receptacle. As a result, the solution proposed by Young is not commercially feasible.

SUMMARY OF THE INVENTION

The present invention addresses the aforedescribed and other disadvantages for modifying a gaseous atmosphere contained within a closed receptacle. More specifically, the present invention addresses the disadvantages associated with the preservation of perishable products by providing a method and apparatus to exchange the gases within said receptacle without inducing distortion or collapse of the receptacle itself. Moreover, the present invention enables gas exchange to be undertaken in an economical and automated fashion which may be accomplished at various levels along the wholesale or retail chain of distribution.

The present invention generally comprises a vacuum chamber provided with a means to move and align a sealed receptacle from a position exterior to the chamber to a desired position within the chamber whereupon the chamber is automatically closed and sealed, a gas exchange probe is automatically inserted into the receptacle through a resealable valve so as to establish flow communication between the interior of the receptacle and the vacuum chamber. The valve is preferably a septum-type valve capable of being penetrated by the probe in a self-sealing relation. A vacuum is then drawn in said chamber thereby evacuating the interior of the receptacle through the gas exchange probe. In such a fashion, distortion or collapse of a flexible receptacle is avoided, since the gas exchange operation does not cause a pressure differential between the interior and exterior of the receptacle.

Gas introduction and exchange is accomplished in a similar manner insofar as the balanced introduction of gas pressure about both the interior and exterior of the receptacle. During the gas reintroduction phase, however, gas introduced into the package may be separately valved from the gas used to repressurize the vacuum chamber. In such a fashion, the exchange gas flows only into the interior of the package, while pressure inside the chamber exterior to the package may be maintained by the introduction of a third gas or even outside air.

The present invention has particular application to the packaging of food products in polystyrene foam or other plastic trays which are hermetically sealed with transparent plastic wrap preparatory to display and marketing. While many other products may be sealed and marketed in this manner, food products require special care in order to preserve both their quality and appearance.

The present invention has a number of advantages over the art. One such advantage is the ability to maintain a minimum pressure differential between the inside and the outside of the receptacle during gas exchange operations. In such a fashion, distortion of the package and liquid purge of the product is minimized.

A second advantage of the invention is the ability to accommodate automated gas exchange operations without the need to reseal the receptacle in a second, separate operation.

Another advantage is the ability to produce a package having a controlled positive pressure so as to reduce or avoid liquid purging as well as other physical aesthetic benefits.

Other objects and advantages of the invention will become apparent from the following detailed description made in conjunction with the accompanying drawings.

BRIEF DESCRIPTION OF THE DRAWINGS

FIG. 1 is a partial cutaway, perspective view of one preferred embodiment of the invention.

FIG. 2 is a side, detail view of the door mechanism illustrated in FIG. 1.

FIG. 3 is a perspective view of a gas exchange apparatus of the present invention as it may relate to one package design.

FIG. 4 is a top, cutaway view of the embodiment illustrated in FIG. 1.

FIG. 5 is a side, detail view of the gas exchange apparatus and accompanying activation means of one embodiment of the invention.

FIG. 6 is a schematic view of one embodiment of the gas exchange apparatus of one embodiment of the invention.

FIG. 10 is a perspective, partially cutaway view of the second embodiment of the invention illustrating the various valving means.

FIG. 11 is a cross sectional view of the evacuation chamber of the embodiment illustrated in FIG. 8.

FIG. 12 is a perspective, detailed view of the gas exchange means of the second embodiment.

FIG. 13 is a side view of the embodiment illustrated in FIG. 8.

FIG. 14 is a perspective, partially exploded view of the seal movement means.

FIG. 15 is a perspective, partially phantom view of the gas exchange means.

FIG. 16 is a detail side view of the gas exchange means and package of the second embodiment of the invention.

FIG. 17 is a perspective view of one preferred embodiment of a product package, where such package includes a seal as applied via the apparatus of the present invention.

FIG. 18 is a perspective, phantom view of the means to lower the tray platform.

FIG. 19 is a perspective, exploded view of yet a third embodiment of the invention.

FIG. 20 is a top view of one embodiment of the application of the apparatus and method of the present invention wherein a plurality of said apparatus are arranged along an endless belt conveyor assembly.

FIG. 21 is a side cutaway view of the second embodiment of the present invention.

FIG. 22 is a perspective, exploded view of the pneumatic activation setup of the embodiment illustrated in FIG. 5.

FIG. 25 is a perspective, detail view of the seal containment assembly.

DESCRIPTION OF THE PREFERRED EMBODIMENT

Figure 7:
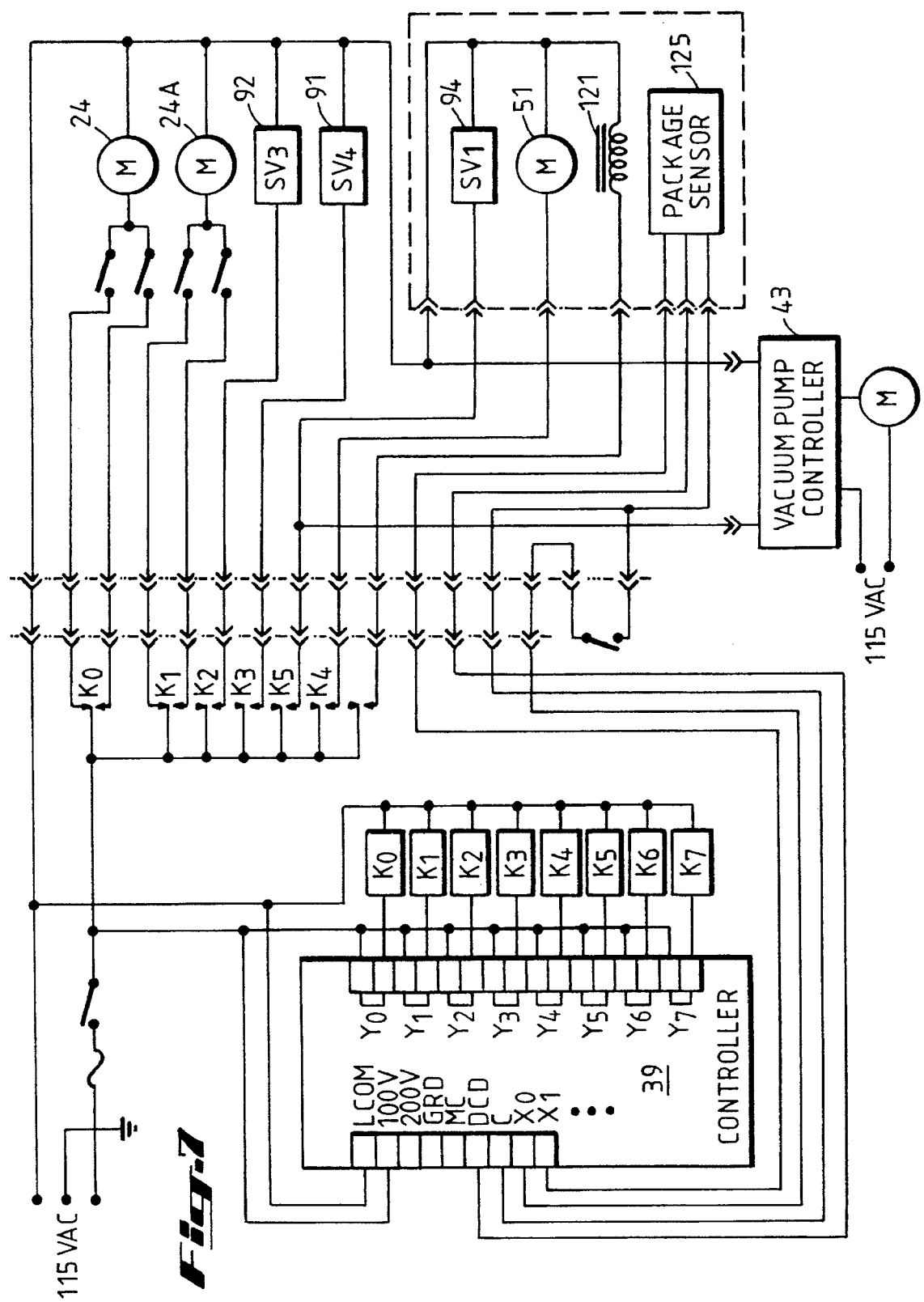
FIG. 7 is a schematic view of the electrical layout of one embodiment of the invention.

One embodiment of the present invention may be seen by reference to FIGS. 1–7.

FIG. 1 illustrates a body 3 supported on a frame 2 wherein body 3 defines a vacuum chamber 6. Chamber 6 is provided with oppositely opposed doors 21 and 21A so as to allow the progressive movement of receptacles or containers 100 therethrough. In the illustrated embodiment, containers 100 are moved along conveyor assembly 4 into and through chamber 6 for purposes of gas exchange and modification as will be further discussed herein.

As illustrated in FIG. 1, conveyor assembly 4 is preferably situated such that it abuts chamber 6 on opposite sides thereof at a height generally compatible with the operation of internal conveyor assembly 83 as will be further described. Assembly 4 may be comprised of a series of rollers 17 linearly assembled along a frame 18 in a generally conventional fashion. Alternatively, assembly 4 may be comprised of a conventional endless track conveyor setup including a conveyor belt and guide rollers (not shown). Ideally, however, assembly 4 should be provided with means to automatically regulate and govern the linear movement of articles placed thereon in a manner compatible with the operation of the gas exchange mechanism as will be below described. In such a fashion, it is preferred that assembly 4 be automatically rather than manually operated.

In the embodiment illustrated in FIG. 1, doors 21 and 21A are pivotally attached to chamber 6 about hinges 7 such that they open in an upward fashion. (See arrow B in FIG. 2). When in a closed position such as that illustrated in FIG. 1, doors 21 and 21A maintain an airtight seal with the body of chamber 6. To accomplish this sealing arrangement, doors 21 are preferably provided with a conventional sealing gasket or the like (not shown) to allow a vacuum to be drawn in chamber 6. Alternately, an appropriate sealing material may be provided on the contact face of chamber 6 receptive to doors 21 when they are situated in a closed position. Doors 21 and 21A are also preferably provided with a locking mechanism of general conventional design to allow for the pressurization of chamber 6.

In the embodiment illustrated in FIGS. 1–7, the operation of doors 21 and 21A is independently controlled by motors 24 and 24A, respectively. Motors 24 and 24A are secured to the top exterior 5 of chamber 6 and are operatively coupled to cam 26 which is rotatably coupled to control arm 22. Control arm 22 is in turn rotatably coupled to door bracket 20, which itself is partially connected to the exterior of chamber 6 as a bracket assembly 9 at one end and to the door at its bottommost extent. In such a fashion, operation of motors 24 and 24A in a "forward" direction results in the upward pivot of doors 21 to an "open" position. Reversal of motors 24 and 24A results in the movement of doors 21 and 21A to a "closed" and locked position. In a preferred embodiment, motors 24 and 24A are electrically coupled to a central control system 39 such as a Toshiba Ex-20 control device in a manner illustrated in FIG. 7. In such a fashion, the operation of doors 21 and 21A may be automatically controlled as will be further discussed herein.

While one preferred embodiment of the invention is illustrated in FIG. 1, other configurations of the present invention are also envisioned in accordance with the spirit of the present invention. For example, the door pivoting arrangement illustrated in FIGS. 1–2 may be replaced with a sliding door mechanism or the like. Similarly, the overall configuration of chamber 6 may also be modified so as to allow for the introduction of a plurality of receptacles 100 of varying sizes. Alternatively, the operation of the doors may be controlled by a single motor in either an independent or dependent fashion. In all embodiments, however, it is desirable that chamber 6 be fashioned of or provided with a transparent panel or "window" so as to allow for visual inspection of the gas exchange operation.

One preferred embodiment of the gas exchange system of the present invention may be seen by reference to FIGS. 1, 4, 5, and 7. FIG. 4 illustrates a top, cutaway view of the interior of chamber 6 revealing a receptacle 100 positioned on an endless track conveyor assembly 83. As illustrated, assembly 83 is comprised of two or more drive rollers 84 and a supporting belt 82. In a preferred embodiment, belt 82 may be made of neoprene or other elastic material, while rollers 84 may be driven by a Dayton Electric 50 RPM, 115 V motor or other comparable drive apparatus. Other conveyance systems are also envisioned and will become obvious to one skilled in the art. It is desirable that any conveyance mechanism be either sealably containable within chamber 6 or otherwise allow for the creation of a vacuum in the chamber.

The gas exchange apparatus of the present invention is designed to be used in association with a presealed receptacle 100 such as that described in applicant's copending application Ser. No. 510,938. As illustrated in FIG. 3, receptacle 100 generally includes a sidewall 19 and a top 21, where the combination forms a sealable, pressurizable unit. In one embodiment, the sidewalls 19 of receptacle 100 may be provided with a resealable valve 102 which may be integrated into the sidewall itself or may be affixed to the surface of the package exterior. In the receptacle 100 illustrated in FIG. 3, valve 102 is prefabricated in a corner of sidewall 19 so as to be compatible with the gas exchange mechanism illustrated in FIGS. 1–7. However, and as will be described below, it is also expressly contemplated that such a valve may be added to the package during the operation of the gas exchange apparatus of the present invention.

To provide for gas exchange, receptacle 100 is preferably aligned on assembly 83 so as to rest flush against a retaining rail 29 and stop 125. Lateral positioning of receptacle 100 along assembly 83 may be accomplished via a flexible alignment arm 80. As illustrated in FIG. 4, arm 80 is situated in chamber 6 so as to be capable of flexure in a plane generally co-planar with that described by assembly 83, and in a lateral direction such as to urge receptacle 80 against retaining rail 29. When compelled by the forward movement of assembly 83 (whose direction of movement is indicted by arrow A) and the lateral force exerted by alignment arm 80, receptacle 100 is moved into an abutting relation with stop 125 and rail 29 as previously described. In this fashion, package valve 102 is positioned immediately proximate gas exchange assembly 120.

In a preferred embodiment, package sensor or control stop 125 is electrically coupled to the central control system 39 as previously described in a manner illustrated in FIG. 7. Actuation of control stop 125 results in the transmission of an electrical signal to control system 39. In a preferred embodiment, stop 125 is pressure activated and thus transmits an electrical signal to control system 39 when contacted by package 100. Preferably, the activation mechanism 51 for conveyor assembly 83 is likewise coupled to control system 39. In such a fashion, when receptacle 100 is moved into contact with stop 125, conveyor assembly 83 is disengaged. Solenoids 121, 94, 91, and 92 are likewise coupled to control system 39 in a manner illustrated in FIG. 7.

The aforedescribed operations have been described as occurring essentially simultaneously. It is envisioned, however, that it may be desirable to provide a programmed or timed delay in the operational sequence of the apparatus.

One embodiment of the gas exchange assembly 120 may be seen by reference to FIGS. 4–5. Gas exchange assembly 120 generally comprises an injector probe 126 mounted on a plunger 123 which is slidably disposed in a housing 125. Probe 126 may be comprised of a fine hollow tube or needle such as a number 20 hypodermic needle manufactured by Becton, Dickinson and Company. Plunger 123 is itself fixedly mounted on the frontal extremity of solenoid 121 as illustrated. Such a solenoid is conventional in design, such as that manufactured by Dayton Electric. Upon activation, solenoid 121 moves injector probe 126 through resealable valve 102 and into communication with the gases sealed within receptacle 100.

Gas exchange assembly 120 is coupled to a three-way valve union 83 via a gas conduit 88. Referring to FIGS. 1, 3 and 4, union 83 allows for the routing of gas flow from and into the interior of receptacle 100. Union 83 is coupled to an evacuation valve 95 via a secondary gas conduit 90. Union 83 is also coupled to a second solenoid 92, such as ASCO Model 826014, via conduit 84. Solenoid 92 is in turn coupled to a gas supply source 40 via conduit 41.

The operation of evacuation valve assembly 95 is controlled by a solenoid 94 such as a Dayton Electric Speedair 2A242. Valve assembly 95 includes a gas inlet 96 which communicates with the interior of chamber 6. Solenoid 94 is electrically coupled to control system 39 and thus may be automatically controlled. When solenoid 94 is activated to an "open" position, gas communication is established between the interior of receptacle 100 and the interior of vacuum chamber 6. When deactivated, solenoid 94 moves to a "closed" position, thereby closing valve 95 and thus preventing the escape or introduction of gas between receptacle 100 and chamber 6. Evacuation of package 100 thus takes place when solenoid 94 is urged to an "open" position.

Repressurization of package 100 takes place when solenoid 94 is situated in a "closed" position.

Chamber 6 is provided with a valving means 101 which enables the removal or addition of gases thereto. Referring to FIGS. 1 and 4, valving means 100 comprises a conduit 99 which is disposed in the sidewall of chamber 6 so as to establish fluid communication therethrough. Conduit 99 is open at its remote end and is coupled to a T 97 at its proximal end. T 97 is also coupled to a solenoid valve 91 and a conduit 98. Solenoid valve 91, when in an "open" position, enables pressurization between the interior and exterior of chamber 6 through nozzle 103. When in a "closed" position, solenoid valve 91 enables a vacuum to be drawn in chamber 6 through conduit 98 which is coupled to vacuum pump 43.

It may sometimes be desirable to remove the atmosphere within container 100 independently of atmosphere removal of chamber 6. This may be necessary when receptacle 100 contains a strong oxidizer, e.g. chlorine or bromine. In such a case, gas removal of receptacle 100 may be conducted via a separate vacuum pump (not shown) coupled, for example, to conduit 84 as indicated by dashed lines 84A. In such a setup, solenoid 94 would be maintained in a "closed" position during the evacuation procedure. Alternatively, structures 94, 95, 96 and coupling 90 would be altogether eliminated.

In cases when receptacle 100 contains a high oxygen content, e.g. >35%, separate gas removal may be carried out via a venturi pump. In such a fashion, the opportunity for explosion or fire is minimized. Evacuation of chamber 6 may be carried out via a faster, conventional vacuum pump as earlier described in reference to the general embodiment.

The operation of the operation illustrated in FIGS. 1–7 be described in sequential fashion as follows. At the completion of the previous gas exchange operation, door 21A is moved to an open position via the activation of motor 24A. Conveyor assembly 83 is likewise activated, thus moving the previous receptacle out of chamber 6. Conveyor track 4, which has likewise been activated, moves the receptacle downstream for packaging or further processing. During this operation, a new receptacle 100 is simultaneously moved into chamber 6 through door 21 which has also been moved to an "open" position. Once package 100 is moved into an abutting relationship with stop 125, door 21A is then moved to a sealed and "closed" position. In a preferred embodiment, movement of receptacle 100 may be automatically controlled as earlier described. Alternatively, the operation of the various separate mechanisms may be conducted via a timed program. Once receptacle 100 has been moved partway into chamber 6, the forward movement of receptacle 100 is completed via the movement of conveyor assembly 83. The operation of assembly 83 moves receptacle 100 into contact with alignment arm 80 which exerts a lateral force on said receptacle. This lateral force, in combination with the forward movement of assembly 83, moves receptacle 100 into contact with retaining rail 19 and stop 125. When contacted by receptacle 100, stop 125 carries an electrical impulse to controller 39 which activates motor 24 which in turn moves door 21 into a closed, sealing position. By a subsequent signal from controller 39, conveyor assembly 83 is then deactivated.

To avoid any problems of contamination which might occur in the event receptacle 100 is damaged or punctured at any time during the gas exchange operation, it is desirable to create a positive pressure inside receptacle 100 prior to the initiation of the gas exchange operation. Accordingly, it is preferred that a partial vacuum be created in chamber 6 prior to gas exchange. Subsequently, therefore, vacuum pump 43 is next engaged and solenoid 91 moved to a "closed" position so as to enable the exhaustion of gas through gas lines 99 and 98. A vacuum or partial vacuum is created immediately prior to the insertion of probe 122 in container 100. Once a vacuum or partial vacuum has been achieved, solenoid 121 is activated, thereby driving probe 122 into receptacle 100 through valve 102 as earlier described. Solenoid 94 is also activated to an "open" position.

The penetration of container 100 by needle 122 enables gas flow through conduit 88 through gas outlet 96 as container 100 is exhausted. Simultaneously, gases within chamber 6 are continuing to be evacuated through inlet 99 via pump 43. In such a fashion, evacuation of chamber 6 results in a simultaneous evacuation of the interior of receptacle 100, thus avoiding any resultant modification in the shape of said receptacle. When a vacuum has been drawn in the interior chamber 6, pump 43 is deactivated, and solenoid 94 is moved to a "closed" position. Actuation of pump 43 and solenoid 94 may be accomplished by vacuum sensors which are activated when a satisfactory vacuum is achieved in chamber 6, or may alternatively be accomplished via the operation of a timer (both not shown).

The present invention has particular application to processes where gas withdrawal and exchange is contemplated. In the event the introduction of a second gas mixture into the receptacle 100 is desired, solenoid 94 is activated to a "closed" position, while solenoid 92 is moved to an "open" position. Gas flow from gas supply 40 may now commence into container 100. Very shortly thereafter, solenoid 91 is activated to an "open" position so as to allow gas flow communication between the interior and exterior of chamber 6. In such a fashion, pressure equalization is thereby maintained between the interior and the exterior of the package 100, thereby eliminating or substantially reducing any collapse. In an alternate embodiment, repressurization of container 100 may be accomplished via a secondary solenoid valve 107 and a pump 192 (see FIG. 6). In such a fashion, more precise pressure regulation may be achieved.

Upon completion of the gas exchange operation, probe 122 is automatically withdrawn from receptacle 100 whereupon assembly 83 is reactivated to move receptacle 100 forward. Concurrently, motor 24A is activated, thus moving door 21A to an open position. Receptacle 100 is then moved forward until it establishes contact with track 4, which automatically moves receptacle 100 downstream for further processing or packaging.

A second embodiment of the present invention is illustrated at FIGS. 8–22.

Figure 8:
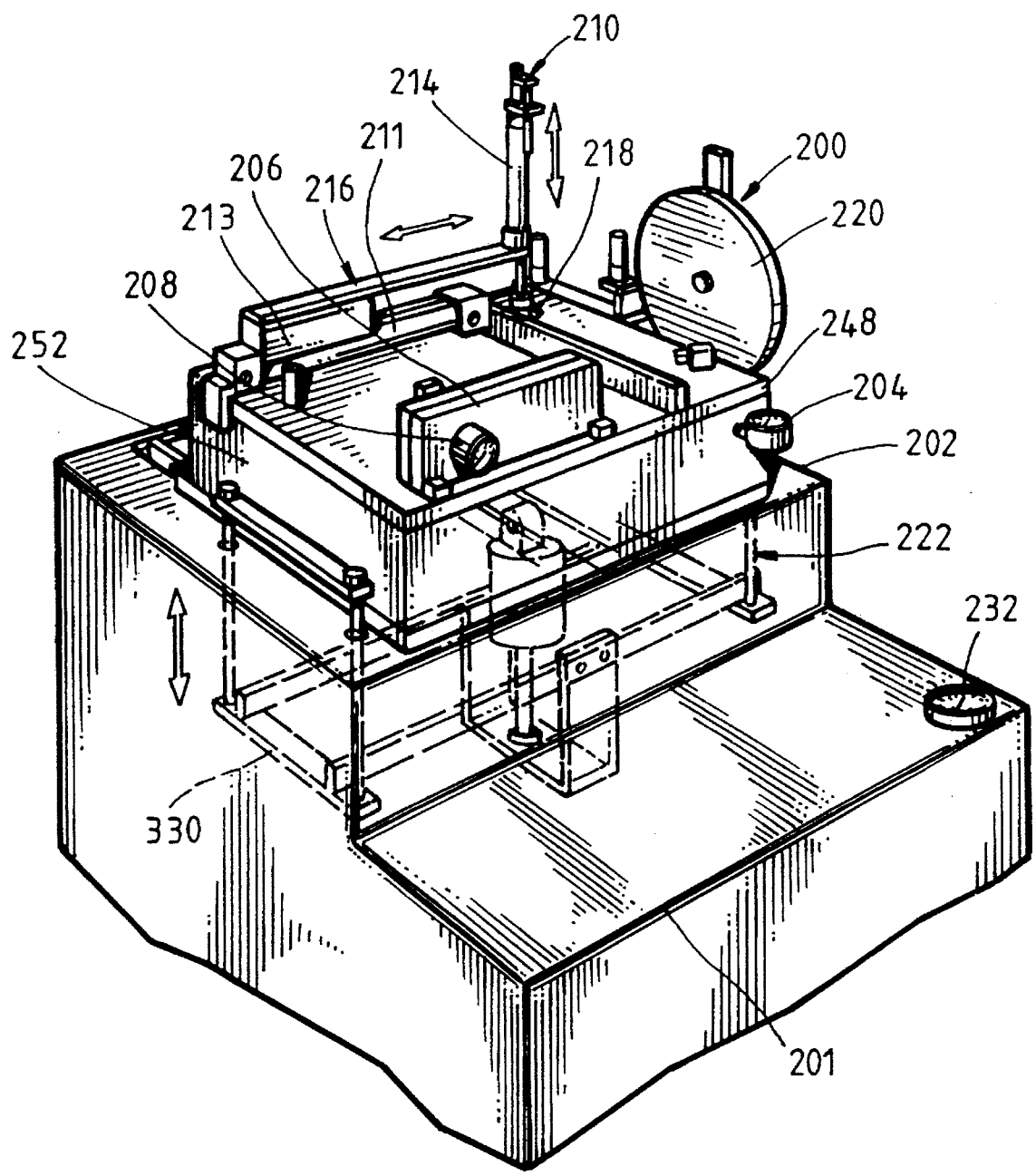
FIG. 8 is a perspective view of a second embodiment of the invention wherein the gas exchange apparatus is illustrated in an activation mode.
Figure 9:
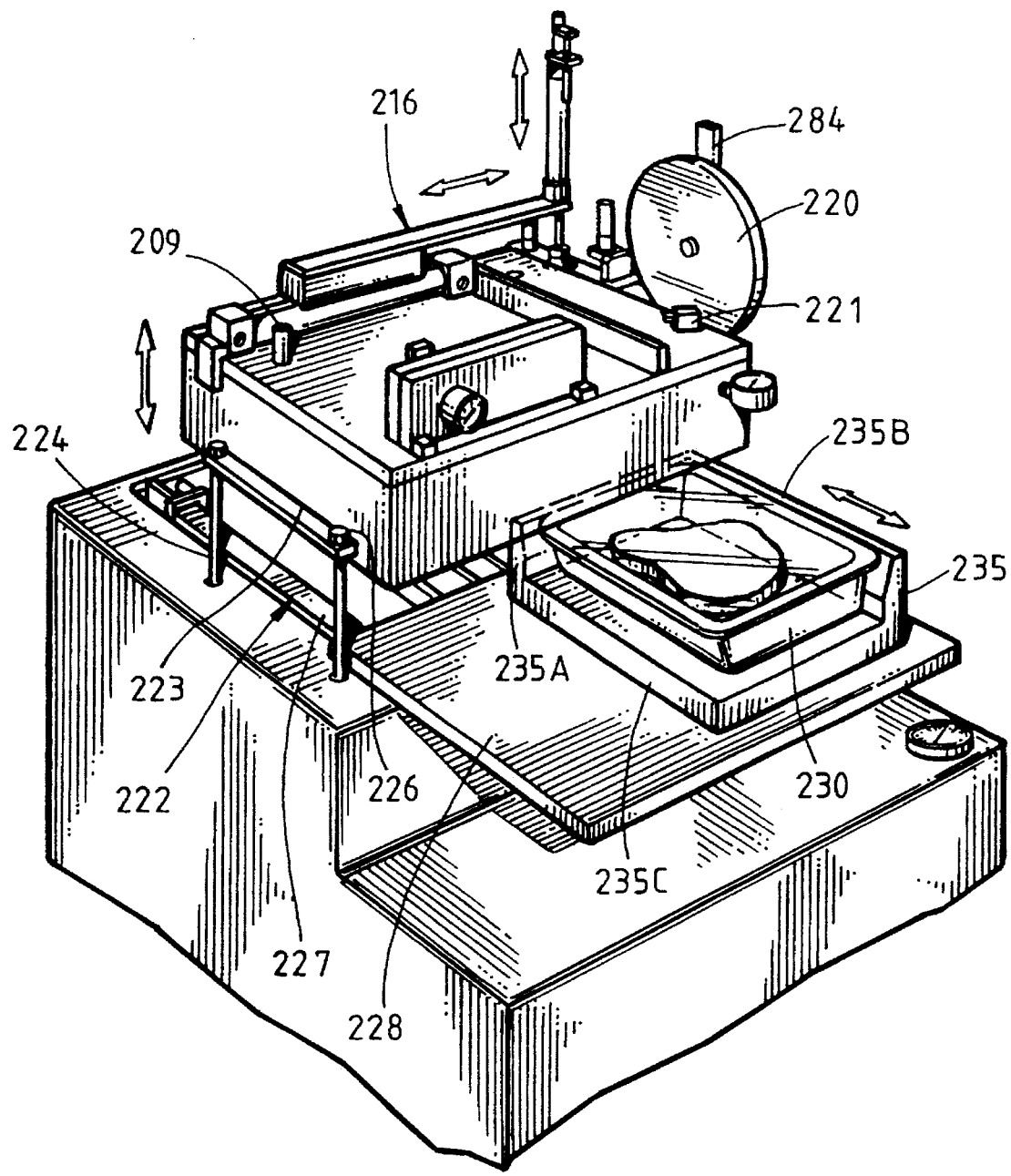
FIG. 9 is a perspective view of an embodiment in a mode to receive a packaged perishable product.

FIGS. 8 and 9 illustrate an overall perspective view of this second embodiment 200 which is generally comprised of a mounting base or frame 201 which defines a chamber or cabinet 258 therein in which is disposed a number of subassemblies to exchange gases from a given package 230. Frame 201 itself supports a subframe 202 as illustrated. Frame 201 and subframe 202 may be formed independently, although a unitary cast or forged construction is also envisioned within the spirit of the present invention.

Referring to FIG. 11, subframe 202 generally comprises four sides 252 and top 248, the combination partially defining a vacuum chamber 258. As illustrated, sides 252 and top 248 are secured together via fasteners 256, although a unitary one-piece design is also contemplated as within the spirit of the present invention. Sides 252 are preferably comprised of a lightweight, strong material, e.g., aircraft grade aluminum or stainless steel, of an appropriate gauge and thickness to withstand the pressures associated with the generation and maintenance of a vacuum in chamber 260. To maintain such a vacuum, o-rings or other appropriate compressible sealing means 254 may be used between the non-integral elements of subframe 202.

Top 248 may be comprised of glass, acrylic or other transparent material to enable viewing of the gas exchange operation within chamber 258 as will be described below. Alternatively, top 248 may be provided with a viewing portal (not shown) to monitor the gas exchange operation. Top is also provided with an access portal 205 to allow insertion of a gas exchange probe 270 as illustrated in FIG. 16 and as will be further described herein.

Referring to FIGS. 9, 18 and 25, a baseplate 228 is slidably mounted to frame 201 and is configured to fit below and form a seal with walls 252 and top 248 so as to form a pressurizable chamber 258. Baseplate 228 is preferably comprised of a material, e.g., aircraft aluminum or steel, capable of maintaining a vacuum within chamber 258 and is transversely moveable relative to frame 201 along guide tracks 227 via linear actuator 336. Linear actuator 336 is situated below and coupled to frame 201 as illustrated.

Baseplate 228 is preferably provided about its upper surface with a package positioning cradle 235, which cradle comprising a backstop 235A, a side stop 235B, and a raised base 235C. The function of positioning cradle 235 is to create an established, repeatable position in said chamber 260 for a package 230 of a given configuration and dimension during the gas exchange operation. In a preferred embodiment, guide tracks 227 are coated with a Teflon or similar coating material having a low coefficient of friction.

Baseplate 228 is moveable between a "load" and a "seal" position. When in a "load" position as illustrated in FIG. 9, baseplate 228 is moved outwardly to accept a given package 230. When the package has been loaded, baseplate 228 is moved inwardly to a "seal" position whereupon it is situated immediately below chamber 258 as formed by walls 252 and top 248. Subframe 202 is then lowered onto baseplate 228 via elevation means 334 so as to form a seal therebetween. To create a sealing engagement between the baseplate 228, walls 252 and top 248, the bottommost portion of walls 252 are preferably provided with a malleable rubber strip or a similar sealing material 254.

Sealing contact between baseplate 228 and elements 252 and 248 is maintained by the downward force created by elevation and seal means 334 as will be described below. Moreover, sealing engagement between these elements is enhanced during the creation of the vacuum in chamber 260 during the gas exchange operation as will also be later described.

Subframe 202 may be raised or lowered with respect to frame 201 via elevation and seal means 222. As illustrated in FIGS. 18 and 25, elevation and seal means 222 is operably coupled to and situated below the surface defined by the top of frame 201 and generally comprises a pneumatic cylinder 382 disposed in a vertical orientation and including a distendable piston 387 coupled to mounting plate 383 and mounting and alignment brackets 385. Brackets 384 are also coupled to a transverse member 384 as illustrated. Mounting and alignment brackets 385 are fixedly coupled to subframe 202 via two pairs of mounting rods 224 which are coupled to mounting brackets 223 which are in turn secured to subframe 202 as illustrated.

Elevation and seal containment means enables the vertical movement of subframe 202 vis-a-vis frame 201. When cylinder 382 is actuated, piston 387 extends downwardly, thus forcing down mounting plate 383 and thus subframe 202 downwardly. When thus downwardly positioned, subframe 202 is compressed downwardly in sealing engagement with baseplate 228. In this position, subframe 202 is situated in a "sealing position" appropriate for commencement of the gas exchange operation. When cylinder 382 is deactivated, plate 383 is returned to its original orientation, thus moving subframe 202 upwardly relative to baseplate 228. In this orientation, the subframe 202 is situated in a "load position."

In the embodiment of the invention illustrated in FIGS. 8–22, it is desirable to affix a gas exchange valve to mass produced, partially rigid prefilled containers during the gas exchange process. In the gas exchange process, a gas exchange septum or valve 299 is applied to the package 230, one embodiment of which is generally illustrated in FIG. 17, and includes a tray bottom 231A and a tray lid 231B, the combination defining a sealable package adapted to contain a perishable product 229 or other item.

During the gas exchange process, a valve 299 is automatically applied to the package lid 231B preliminary to the exchange of gases within package 230, which valve 299 is adapted to remain on and maintain the gas tight integrity of said package 230 at the completion of the gas exchange operation. It is expressly contemplated that valve 299 will be comprised of a resilient material, e.g., latex, which can be punctured by a needle or probe, and thereafter expand to reseal the opening created by said puncture. In a preferred embodiment, each of valves 299 may be disposed on a reel of backing film 300 in an end-to-end relationship as illustrated in FIG. 13. It is envisioned that such valves would be manufactured from a type of latex or other elastic material which is perforated into sections of an appropriate size.

In the present invention, valves 299 are applied to package 230 via an automatic feed and seal means 215 which is illustrated in FIGS. 13–14 and 23–24. FIG. 13 is a side view of the subframe 202 and illustrates various components of feed and seal means 215 which generally comprises a reel off spool 220 and an advancement assembly 206. Spool 220 is adapted to hold a wound reel of valves 229 as earlier described, and may be coupled to subframe 202 via an upright bracket 284 and pin 286.

Referring to FIGS. 13–14 and 23–24, advancement assembly 206 includes a pinch bracket 312 and first and second movement means 219 and 273, respectively. Pinch bracket 312 defines about its middle a depression or cup 320. Cup 320 is configured to accommodate probe 214 will be further described below. First and second movement means include pneumatic cylinders positioned in a vertical orientation relative to subframe 202 as illustrated. Pinch bracket 312 includes a first end 314 and a second end 316, and is disposed atop a tape travel bed defined by a first support 280 which in turn is secured to subframe 202. First end 314 is coupled to second support 293 and fastener 302, which fastener 302 enables pinch bracket 312 to pivot thereabout in a vertical plane as indicated by arrow "A" in FIG. 14. Second end 316 is coupled to pivot arm 306 which is in turn coupled to second movement means 273 which enables second end 316 to pivot about fastener 302 as above described. The first end 316 of pinch bracket 312 is coupled to second movement means 272 via pivot arm 306 and fasteners 307 and 308. Second movement means 273 is coupled to a pressurized air supply via high pressure line 274. (See FIG. 13).

First and second supports 280 and 293 are slidably coupled to stationary supports 285 and 292 via track 283 as illustrated via movement means 296. Movement means 296 comprises a pneumatically actuated cylinder 296 and is horizontally disposed between stationary support 292 and first support 280. When actuated, cylinder 296 causes the horizontal movement of pinch bracket 312 over the tape travel bed as above described.

In the illustrated embodiment, the terminal second end 316 of pinch bracket 312 is configured to receive tension maintenance member 324 in a dovetail relationship. Tension maintenance member 324 is fixedly coupled to bracket 285, and is configured at its bottom side to receive a continuous progression of valve elements 299 in an end-to-end relationship as above-described and as illustrated in FIGS. 13 and 14. In this connection, member 324 when coupled to bracket 285, defines a channel therebetween to accommodate the progression of valve elements 299 so as to maintain tension in said elements during the operation of the advancement assembly 215 as will be described herein. To avoid jamming of means 215, it may be desirable to include a roller guide 287 or other similar means at the inlet to member 324 as illustrated in FIG. 14.

First movement means 219 is likewise comprised of a pneumatic cylinder 221 which is fixedly coupled at its bottom terminal end to a stationary support 292. Cylinder 219 is coupled at its upper end to a high pressure air line 207. Actuation of cylinder 221 results in the extension of a securing arm 269 which prevents the longitudinal movement of the valve tape 300 by securing it against the top of fixed member 292.

Figure 23:
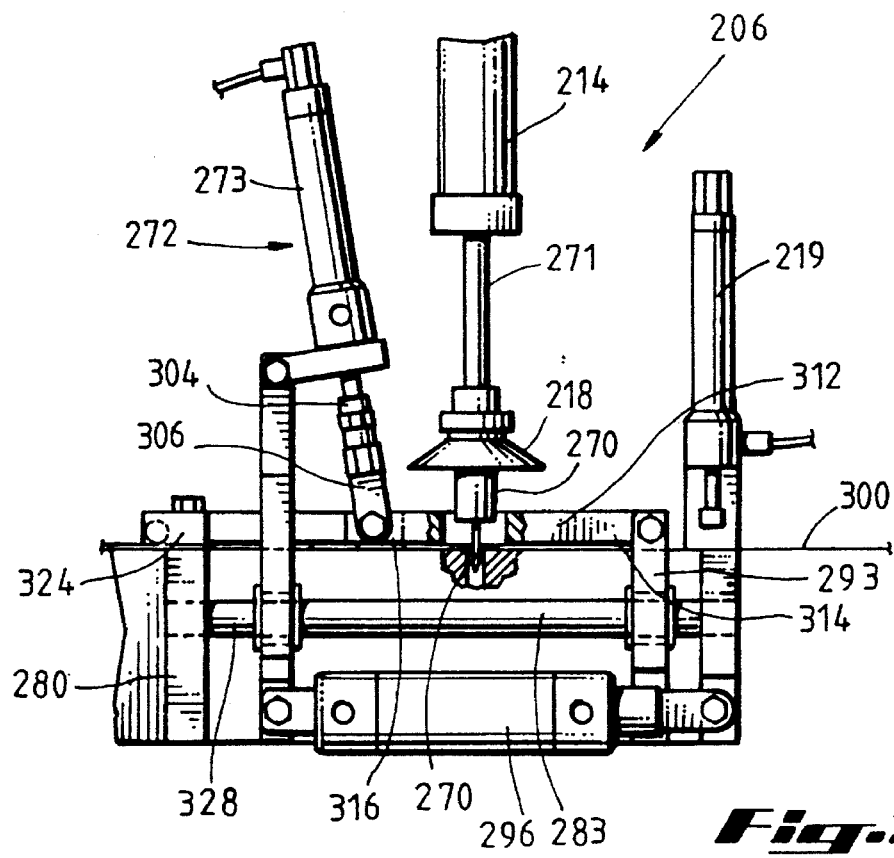
FIG. 23 is a detail side view of the valve advancement assembly.
Figure 24:
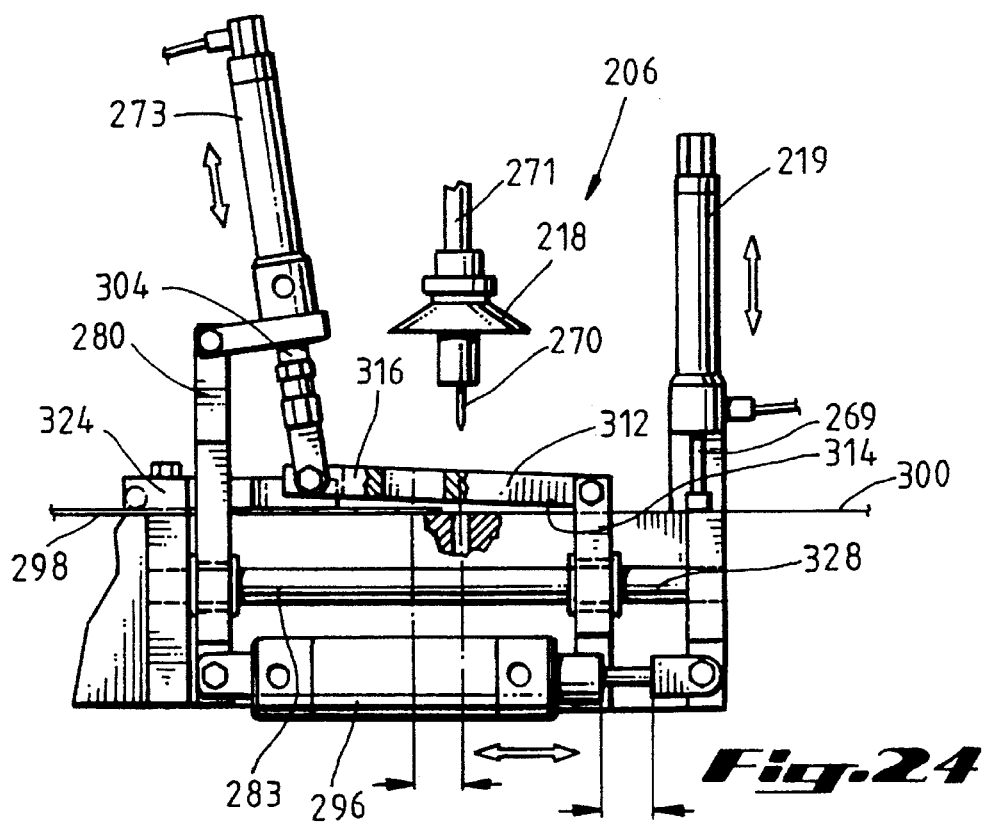
FIG. 24 is a second view of the valve advancement assembly.

The operation of the valve advancement assembly may be described as follows. Flexible valves 299 disposed in an end-to-end relation on a paper tape 300 are carried on reel 220, the free end of which valve tape 298 being threaded through advancement assembly 272 as illustrated in FIGS. 13, 14, 23 and 24. In a "first" position as illustrated in FIG. 23, second movement means 273 is actuated, thus forcing pinch plate 312 over the valve tape 298. In this position, movement means 296 is situated in a nonactuated position as is first movement means 219. In this "first" position, valves 299 may be removed from the tape strip 300 as will be further described in association with gas exchange operation. In a second position as illustrated in FIG. 24, second movement means 273 is deactuated, thus resulting in an upward pivot of pinch plate 312. In the "second" position as illustrated in FIG. 24, movement means 296 is actuated, thus resulting in a horizontal movement of valve tape 298 along the tape travel bed. In the "second" position, first means 219 is actuated, thus holding the free tape end 300.

An alternate embodiment of the advancement assembly is illustrated in FIG. 19 in which is disclosed a base 367 to which are coupled a mounting bracket 368 and a tension plate 373, said plate 373 configured along its bottom side to allow for the movement of a valve tape therethrough. The valve tape 378 contemplated for use with this embodiment includes a number of apertures 379 about one or both sides of a middle track bearing a number of valves 375 situated on an adhesive backing 380 in an end-to-end relationship as earlier described. Valves 375 are also preferably of the same material and manufacture as earlier described.

The progression of valve tape 378 along base 367 is accomplished via the interaction of a tape advance means 374 which comprises a rotary spindle 381 horizontally disposed relative to base 367 in a mounting hub 377. Spindle 381 preferably includes a series of toothed cogs 376 which are compatible with apertures 379 as illustrated. Spindle 381 is rotated via a conventional drive system (not shown).

Referring to FIGS. 12, 13, 15 and 16 there is illustrated a gas exchange assembly 210 generally comprising a pneumatic cylinder 214 coupled at its upper end to a hollow connecting conduit 260 which in turn is coupled to a supply of pressurized gas via flexible conduit 234. Assembly 210 also includes a first and second alignment brackets 266 and 268 and alignment rod 264, the combination allowing lower bracket 266 to move in a fixed vertical relationship via upper bracket 268 while preventing relative rotation of the two members. At its lower end, cylinder 214 is fixedly coupled to bracket 217 which in turn is slidably coupled to subframe 202 as will be described below. At its lowermost extent, assembly 210 includes a probe sleeve or sheath 271, containment cup 218 and probe 270. Probe 270 is slidably disposed within sleeve 271 and is responsive to cylinder 214. When cylinder 214 is actuated, probe 270 is moved to a downward orientation. Probe 270 defines a hollow base therethrough to allow for gas communication via gas conduit 234.

Gas exchange assembly 210 is adapted to be positioned vis-a-vis subframe 202 and package 230 which is disposed in chamber 260. This positioning is created by movement of assembly 210 in at least two planes. Movement of assembly 210 in a vertical plane has been described above. By reference to FIGS. 8–10, gas exchange assembly 210 is adapted to move transversely with respect to subframe 202 via movement assembly 216. Movement assembly 216 includes a bracket 240 which is coupled to a carriage 213 which is slidably disposed on track 217 which is itself secured to the upper surface of subframe 202.

The interaction of the gas exchange assembly 210 and advancement assembly 206 may be described as follows. To collect a valve element 299, assembly 210 is moved to an "outboard" position along track 217. In the outboard position, assembly 210 is positioned precisely over the cup 320 defined in pinch plate 312. When thusly positioned, cylinder 214 is actuated, thereby moving sheath 271, containment cup 218 and gas exchange probe 270 downwardly until probe 270 contacts and punctures one of the valves 299 which is held in a taut relationship vis-a-vis said probe 270 via pinch plate 312 and tension maintenance member 324 as earlier described.

When said probe 270 has penetrated said valve, cylinder 214 is again actuated, thereby returning sheath 271 and probe 270 to their original upright position. Upon such upward movement, valve 299, impaled on probe 270, is removed from tape strip 300. Assembly 210 is then moved to a second "gas exchange" position over the access aperture 205 formed in the top 248 of subframe 202. Cylinder 214 is again actuated, thereby lowering probe 270 into a downward position via subframe 202 such that containment cup 218 firmly engages and forms a seal with the upper surface of top plate 248 over aperture 205. When probe 270 is moved downwardly through aperture 206, valve 299 which is still impaled on probe 270, is moved into chamber 258.

When a seal is established between cup 218 and top plate 248, chamber 258 is evacuated via a high pressure gas line 209. Immediately after the evacuation of chamber 258 is commenced, probe 270 is moved through the material forming the lid 231B of tray 231 to a sufficient extent such that the preadhesive bottom side of valve 299 engages lid 231B. Evacuation of the interior of package 230 is then commenced through probe 270 and gas conduit 234. When evacuation of package has been completed, a second gas or gas mixture may be reintroduced in the package.

At the conclusion of the gas exchange operation, cylinder 214 is again actuated thereby returning probe 270 to an elevated position vis-a-vis subframe 202. Valve 299, however, remains fastened to package lid 231B thereby maintaining the gas mixture therein.

It is expressly contemplated that the aforereferenced operation be conducted automatically in a series of preprogrammed steps. In this connection, it is envisioned that the second embodiment may utilize a conventional onboard computer (not shown). Alternately, the operation may be governed mechanically.

What I claim is:

1. A method for replacing a first gas contained within a sealed receptacle containing a food product with a second gas, comprising the sequential steps of:
    (a) placing the sealed receptacle containing said product in a chamber capable of maintaining a desired pressure on said receptacle;
    (b) placing the receptacle in fluid communication with the interior of said chamber through a self-sealing resealable valve so as to equalize the pressure therebetween while otherwise maintaining the sealed condition of said receptacle where said fluid communication occurs within said chamber;
    (c) Drawing a first partial vacuum in said chamber so as to remove the first gas from said receptacle through the self-sealing valve;
    (d) injecting an oxidizing gas into said receptacle while separately injecting a second gas into said chamber so as to equalize the pressure between the interior of the receptacle and the interior of the chamber;
    (e) placing the receptacle containing the oxidizing gas in fluid communication with said chamber through the self-sealing valve;
    (f) drawing a second partial vacuum in said chamber so as to substantially remove the oxidizing gas from the receptacle through the self-sealing valve;
    (g) injecting a third has in said receptacle through the self-sealing valve while separately injecting the second gas into said chamber so as to again equalize the pressure between the interior or the receptacle and the interior of the chamber; and
    (h) removing the equalized receptacle containing the third gas from the chamber.

2. The method of claim 1 wherein a partial vacuum is drawn in the chamber immediately prior to placing the receptacle in fluid communication with the interior of the chamber.

3. The method of claim 1 wherein the oxidizing gas includes $O^3$.

4. The method of claim 3 where the third gas is inert to the product.

5. The method of claim 4 wherein the third gas comprises $CO_2$.

6. A method for replacing a first gas contained within a sealed, receptacle with a second gas, while maintaining the structural integrity of said receptacle, the method comprising the sequential steps of:
    (a) placing the sealed receptacle in a vacuum chamber;
    (b) evacuating the first gas contained in the receptacle into the chamber through a resealable valve disposed in said receptacle while simultaneously evacuating said chamber;
    (c) introducing a second gas into the evacuated receptacle through said resealable valve while simultaneously introducing a third gas into the evacuated chamber at a rate so as to substantially eliminate any pressure differential between the interior of said receptacle and the interior of said chamber.

7. The method of claim 6 wherein said second gas is inert.

8. The method of claim 7 wherein said inert gas includes $CO_2$.

9. The method of claim 6 wherein said second gas includes an oxidizer.

10. The method of claim 6 wherein said oxidizer includes ozone gas.

11. An apparatus for removing a first gas surrounding a given material in a sealed receptacle and exchanging said first gas with a second gas so as to avoid the collapse or loss of structural integrity in said receptacle during such exchange, comprising:
    (1) a vacuum chamber for maintaining a controlled pressure and environment about said receptacle;
    (b) valve means to selectively enable gas communication between the interior of said receptacle and the interior of said chamber;
    (c) means to evacuate said receptacle through said valve means into said chamber and to simultaneously evacuate said chamber at a rate to control the pressure differential between the inside and the outside of the receptacle;
    (d) means to introduce a second gas into the evacuated receptacle while simultaneously introducing a third gas into the evacuated chamber.

12. The apparatus of claim 11 further comprising a hollow probe between the valve means and the receptacle operable in a first condition to communicate between the valve means and the receptacle and in a second condition between the receptacle and the exterior of the chamber.

13. The apparatus of claim 12 which further comprises a septum valve in said receptacle adapted to receive said hollow probe.

14. Apparatus adapted to remove, modify, or exchange a first gas contained within a sealed flexible receptacle provided with a resealable valving means maintaining a positive pressure within said receptacle, comprising:
    (a) a sealable, pressurizable chamber adapted to receive said receptacle;
    (b) a probe automatically insertable through said valving means upon such receipt of said receptacle in said chamber;
    (c) selective valving means operable in a first condition to enable gas communication between the interior of said chamber and the interior of said receptacle, and in a second condition between the interior of said receptacle and a source of gas; and
    (d) means to evacuate said receptacle through said valving means into said chamber and to simultaneously evacuate said chamber at a rate to control the pressure differential between the inside and outside of the receptacle.

15. Apparatus adapted to remove, modify, or exchange a first gas contained within a sealed receptacle while maintaining a positive pressure in said receptacle, comprising:
    (a) a vacuum chamber provided with a sealable entrance and exit;
    (b) a conveyor assembly sealably disposed in said chamber and operable to move said receptacle sequentially from said entrance to said exit;
    (c) a hollow insertion probe rigidly coupled to a solenoid such that activation of said solenoid moves said probe through said receptacle into fluid communication with the interior of said receptacle and thereby forming an aperture in said receptacle, said probe being coupled to valving means to selectively enable gas communication between the interior of said receptacle and the interior of said vacuum chamber in a first condition, and in a second condition to allow gas communication between the interior of said receptacle and a supply of gas; where said valving means is actuated via a second solenoid;

(d) a chamber valve adapted to evacuate said chamber; and (e) means to affix a resealable valve over said aperture in said receptacle to allow for the further gas exchange of the receptacle therethrough.

16. A method of treating a product which has been placed on a plastic tray and hermetically sealed with a transparent plastic wrap, which comprises the sequential steps of:

(a) providing the wrapped tray with a self-sealing valve;

(b) placing the wrapped tray with the self-sealing valve in a vacuum chamber;

(c) closing the vacuum chamber;

(d) establishing fluid communication between the chamber and the interior of the wrapped tray through the self-sealing valve where said fluid communication is accomplished within said chamber;

(e) evacuating the vacuum chamber at a rate consistent with maintaining substantially equal pressures within the chamber and the wrapped tray through the self-sealing valve;

(f) interrupting fluid communication between the chamber and the interior of the wrapped tray;

(g) supplying a first gas through the self-sealing valve into the evacuated wrapped tray separately from the chamber, and contemporaneously supplying a second gas into the evacuated chamber separately form the wrapped tray at a rate consistent with maintaining substantially equal pressures within the chamber and the wrapped tray; and (h) interrupting the flow of said first and second gases.

17. The method of claim 16 which further comprises separately evacuating the wrapped tray and the chamber, after the interruption of the flow of said first and second gases at rates consistent with maintaining substantially equal pressures between the chamber and the wrapped tray.

18. The method of claim 17 which further comprises:

(a) supplying a third gas through the self-sealing valve into the wrapped tray after evacuation of the first gas, and contemporaneously supplying another gas into the evacuated chamber separately from the wrapped tray at a rate consistent with maintaining equal pressures within the chamber and the wrapped tray; and (b) interrupting the flows of said third gas and said other gas.

19. Apparatus for treating a food product packaged on a plastic tray and hermetically sealed with plastic wrap which comprises:

(a) a vacuum chamber adapted to receive such a package at a first end and discharge the package at a second end;

(b) closure means at said first and second ends operable to seal said vacuum chamber:

(c) guide means within said chamber operable to guide such packages of various sizes into a position within said chamber, such that septum valves of the various size packages engage a common point of the chamber;

(d) a hollow gas exchange probe operable when the septum valve contacts said common point to penetrate the septum valve pierce said plastic wrap and affix said valve over the resulting aperture in said wrap;

(e) a forked conduit connecting said probe via a first fork to the interior of said chamber and via a second fork to the exterior of said chamber;

(f) a first valve in said first fork; and (g) a second valve operable to selectively connect the interior of said chamber to the interior of said package.

20. The apparatus of claim 19 which further comprises a vacuum pump positioned external of the chamber and connected to said second valve.

21. The apparatus of claim 20 which further comprises a source of gas positioned external of the chamber and connected to the second fork of the forked conduit.

22. An apparatus for automatically exchanging a first gas in a sealed receptacle with other gases so as to avoid both the collapse of said package and the loss of a seal between the interior and exterior of the receptacle, comprising:

(a) a vacuum chamber for maintaining a controlled pressure about said receptacle;

(b) means to selectively enable gas communication between the interior of said receptacle and the exterior of said chamber, which means includes submeans to puncture said tray and then affix a valve over the aperture created by said puncture; and (c) means to simultaneously evacuate said receptacle through said valve means and said chamber at a rate to control the pressure difference between the inside and outside of said receptacle.

23. A method for replacing a first gas contained within a sealed receptacle containing a perishable product with a second gas, comprising the steps of:

(a) placing the sealed receptacle containing said product in a chamber capable of maintaining a desired pressure on said receptacle;

(b) sealing said chamber;

(c) forming an aperture in said receptacle and affixing a resealable valve over said aperture after said receptacle is inserted in said chamber, and placing said receptacle in fluid communication with the exterior of said chamber through said resealable valve;

(d) removing said first gas from said receptacle while depressurizing said chamber such that the pressure maintained in said receptacle is slightly greater than the pressure maintained in said chamber;

(e) injecting a second gas into said receptacle through said valve while pressurizing said chamber such that the pressure maintained in said receptacle is slightly greater than the pressure in said chamber;

24. The method of claim 23 wherein said second gas includes an oxidizer.

25. The method of claims 23 wherein the oxidizing gas is drawn from a group comprising $O_3$, $Cl_2$, and $Br_2$.

26. The method of claim 23 wherein said resealable valve is placed over said aperture by a hollow probe, wherein said probe both forms said aperture and further serves as a gas exchange conduit.

27. A method for replacing a first gas contained within a sealed receptacle containing a perishable product with a second gas, comprising the steps of:

(a) placing the sealed receptacle containing said product in a chamber capable of maintaining a desired pressure on said receptacle;

(b) sealing said chamber;

(c) forming an aperture by a hollow probe in said receptacle and affixing a resealable valve over said aperture after said receptacle is inserted in said chamber, and placing said receptacle in fluid communication with the exterior of said chamber through said resealable valve where said probe both forms the aperture and serves as a gas exchange conduit;

(d) removing said first gas from said receptacle while depressurizing said chamber such that the pressure maintained in said receptacle is slightly greater than the pressure maintained in said chamber;

(e) injecting a second gas into said receptacle through said valve while pressurizing said chamber such that the pressure maintained in said receptacle is slightly greater than the pressure in said chamber.

* * * * *